(12) United States Patent
Goto et al.

(10) Patent No.: US 10,206,917 B2
(45) Date of Patent: Feb. 19, 2019

(54) AQUEOUS DRUG

(71) Applicant: KYORIN PHARMACEUTICAL CO., LTD., Tokyo (JP)

(72) Inventors: Takahiro Goto, Tochigi (JP); Hitoshi Kozuka, Tochigi (JP); Mizuho Shibata, Tochigi (JP); Wataru Minagawa, Tochigi (JP); Norihiro Kanayama, Tochigi (JP); Chifuyu Toriumi, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/578,758

(22) PCT Filed: Jun. 2, 2016

(86) PCT No.: PCT/JP2016/066410
§ 371 (c)(1),
(2) Date: Dec. 1, 2017

(87) PCT Pub. No.: WO2016/195020
PCT Pub. Date: Dec. 8, 2016

(65) Prior Publication Data
US 2018/0169088 A1    Jun. 21, 2018

(30) Foreign Application Priority Data

Jun. 2, 2015   (JP) .................................. 2015-111863

(51) Int. Cl.
*A61K 31/44* (2006.01)
*A61K 31/4709* (2006.01)
*A61K 9/08* (2006.01)

(52) U.S. Cl.
CPC ............ *A61K 31/4709* (2013.01); *A61K 9/08* (2013.01)

(58) Field of Classification Search
CPC .................................................. C07D 471/04
USPC ............................................... 514/300, 312
See application file for complete search history.

(56) References Cited

U.S. PATENT DOCUMENTS

| 5,304,559 | A | 4/1994 | Rozier |
| 5,334,589 | A | 8/1994 | Al-Razzak et al. |
| 5,811,130 | A | 9/1998 | Boettner et al. |
| 6,288,080 | B1 | 9/2001 | Barsuhn et al. |
| 9,328,089 | B2 * | 5/2016 | Araya ................. C07D 401/04 |
| 2004/0082593 | A1 | 4/2004 | Sommermeyer et al. |
| 2006/0281779 | A1 * | 12/2006 | Asahina ............... C07D 401/04 |
| | | | 514/300 |
| 2009/0117205 | A1 | 5/2009 | Yano et al. |
| 2016/0067185 | A1 | 3/2016 | Uchida et al. |
| 2016/0074330 | A1 | 3/2016 | Uchida et al. |

FOREIGN PATENT DOCUMENTS

| JP | 63-188626 | 8/1988 |
| JP | 2-264724 | 10/1990 |
| JP | 4-230631 | 8/1992 |
| JP | 2003-226643 | 8/2003 |
| JP | 2004-509921 | 4/2004 |
| WO | 91/09525 | 7/1991 |
| WO | 97/23217 | 7/1997 |
| WO | 99/29322 | 6/1999 |
| WO | 2005/026147 | 3/2005 |
| WO | 2006/004028 | 1/2006 |
| WO | 2014/174846 | 10/2014 |
| WO | 2014/174847 | 10/2014 |

OTHER PUBLICATIONS

Alarcon et al., Magnes Res, 2014, 27(2): 57-68.*
International Search Report dated Jul. 12, 2016 in International (PCT) Application No. PCT/JP2016/066410.
International Preliminary Report on Patentability dated Dec. 5, 2017 in International (PCT) Application No. PCT/JP2016/066410.

* cited by examiner

*Primary Examiner* — Rei Tsang Shiao
(74) *Attorney, Agent, or Firm* — Wenderoth, Lind & Ponack, L.L.P.

(57) ABSTRACT

An aqueous drug that contains the compound represented by formula (1) or a salt thereof and in which the precipitation and the chemical dissolution of the compound of formula (1) or of a salt thereof is inhibited. An aqueous drug containing: the compound represented by formula (1) or a salt thereof; and a magnesium compound. The aqueous drug has a pH of 5.8-6.9. The concentration of the compound represented by formula (1) is 3 mg/mL or more.

10 Claims, 2 Drawing Sheets

FIG.2

| No. | 2θ | RELATIVE INTENSITY | INTENSITY |
|---|---|---|---|
| 1 | 8.8 | vs | 3043 |
| 2 | 9.8 | m | 872 |
| 3 | 10.8 | s | 1715 |
| 4 | 11.6 | s | 2236 |
| 5 | 12.9 | s | 2406 |
| 6 | 13.2 | m | 821 |
| 7 | 14.4 | m | 1205 |
| 8 | 14.7 | s | 1913 |
| 9 | 15.7 | m | 778 |
| 10 | 15.8 | m | 940 |
| 11 | 16.4 | m | 945 |
| 12 | 16.9 | m | 772 |
| 13 | 17.1 | m | 717 |
| 14 | 17.3 | m | 1140 |
| 15 | 18.3 | s | 2078 |
| 16 | 18.5 | w | 483 |
| 17 | 19.3 | w | 210 |
| 18 | 19.5 | m | 528 |
| 19 | 19.7 | m | 616 |
| 20 | 19.9 | w | 302 |
| 21 | 20.2 | m | 718 |
| 22 | 21.2 | s | 1990 |
| 23 | 21.6 | m | 1335 |
| 24 | 21.7 | s | 2181 |
| 25 | 22.4 | m | 767 |
| 26 | 23.4 | m | 1383 |
| 27 | 23.9 | m | 982 |
| 28 | 24.2 | m | 833 |
| 29 | 24.4 | s | 2083 |
| 30 | 25.0 | m | 1038 |
| 31 | 25.3 | w | 470 |
| 32 | 25.5 | m | 695 |
| 33 | 25.8 | m | 863 |
| 34 | 26.0 | m | 997 |
| 35 | 26.4 | s | 2030 |
| 36 | 26.8 | m | 1677 |
| 37 | 27.3 | m | 982 |
| 38 | 27.8 | m | 715 |
| 39 | 28.3 | m | 717 |
| 40 | 29.0 | w | 385 |
| 41 | 29.5 | m | 610 |
| 42 | 30.3 | w | 330 |
| 43 | 31.6 | m | 615 |
| 44 | 32.2 | m | 665 |
| 45 | 32.5 | w | 405 |
| 46 | 32.8 | m | 843 |
| 47 | 33.1 | w | 402 |
| 48 | 33.6 | m | 835 |
| 49 | 34.0 | w | 332 |
| 50 | 34.4 | w | 338 |
| 51 | 34.8 | m | 595 |
| 52 | 35.4 | m | 510 |
| 53 | 36.1 | w | 385 |
| 54 | 36.5 | w | 453 |
| 55 | 36.8 | w | 435 |
| 56 | 39.0 | m | 625 |
| 57 | 39.3 | w | 380 |

DEFINITION
% RELATIVE INTENSITY (ri)

| | DEFINITION |
|---|---|
| $20 \leq ri \leq 100$ | vs (VERY STRONG) |
| $20 \leq ri < 50$ | s (STRONG) |
| $5 \leq ri < 20$ | m (MODERATE) |
| $0.7 \leq ri < 5$ | w (WEAK) |
| $ri < 0.7$ | vw (VERY WEAK) |

AQUEOUS DRUG

TECHNICAL FIELD

The present invention relates to an aqueous liquid formulation. More specifically, the present invention relates to an aqueous liquid formulation including a solution that contains a compound represented by general formula (1) (hereinafter, also referred to as a compound of formula (1)) or a salt thereof, and a magnesium compound.

[Chemical Formula 1]

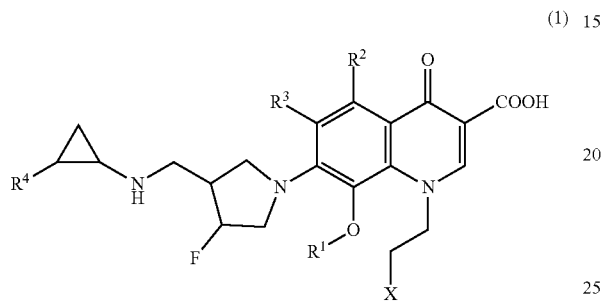

(1)

In the formula (1), $R^1$ represents an alkyl group having 1 to 3 carbon atoms which is optionally substituted with one or more substituents selected from the group consisting of a hydrogen atom, a halogen atom, an amino group, a cyano group, or a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom.

BACKGROUND ART

It is known that a 7-[4-substituted-3-{(cyclopropylamino)methyl}-1-pyrrolidinyl]quinolone carboxylic acid derivative not only is safe and has a strong antibacterial activity, but also exhibits a strong antibacterial activity to resistant bacteria such as methicillin-resistant *Staphylococcus aureus* (MRSA), penicillin-resistant *Streptococcus pneumoniae* (PRSP), and vancomycin-resistant *Enterococcus* (VRE) (Patent Literature 1).

An aqueous liquid formulation having a pH that is higher or lower than the physiological pH sometimes provides stimuli when administered. Hence, it is preferable to design an aqueous liquid formulation which has a pH around the physiological pH, that is, a near-neutral pH, when designing an aqueous liquid formulation such as an injectable formulation. Patent Literatures 2 to 7 disclose an aqueous liquid formulation in which a quinolone carboxylic acid derivative is contained as a principal agent and which is neutral pH. These literatures disclose a formulation in which the precipitation of the principal agent is suppressed and the principal agent is solubilized by adding polyvalent metal such as magnesium into a solution (Patent Literatures 2 to 7).

On the other hand, there is known an aqueous liquid formulation in which a solution containing a quinolone carboxylic acid derivative as a principal agent is adjusted to be slightly acidic, around pH 4, thereby to improve the chemical and physical stability of the principal agent (Patent Literatures 8 to 9). Patent Literature 9 discloses a formulation which includes a lyophilized formulation containing quinolone carboxylic acid and a dilution liquid containing a polyvalent metal compound.

It is noted that the above-described quinolone carboxylic acid derivative disclosed in Patent Literatures 2 to 9 does not have a cyclopropylaminomethyl structure.

CITATION LIST

Patent Literature

Patent Literature 1: WO2005/026147
Patent Literature 2: WO1991/009525
Patent Literature 3: WO1997/023217
Patent Literature 4: WO1999/29322
Patent Literature 5: JP1988-188626
Patent Literature 6: JP1992-230631
Patent Literature 7: JP1990-264724
Patent Literature 8: JP2004-509921
Patent Literature 9: WO2006/004028

SUMMARY OF INVENTION

Technical Problem

An object is to provide a novel aqueous liquid formulation that contains a compound of formula (1) or a salt thereof, in which the chemical decomposition of the compound of the formula (1) or a salt thereof is inhibited.

Solution to Problem

The present inventors intensively conducted research on the preparation of the aqueous liquid formulation that contains the compound of the formula (1) or a salt thereof. As a result, they determined that the cyclopropylaminomethyl structure contained in the compound of the formula (1) is likely to be chemically decomposed, causing the generation of a compound represented by general formula (2) (hereinafter, also referred to as a "compound of formula (2)") in which a cyclopropyl group is detached.

[Chemical Formula 2]

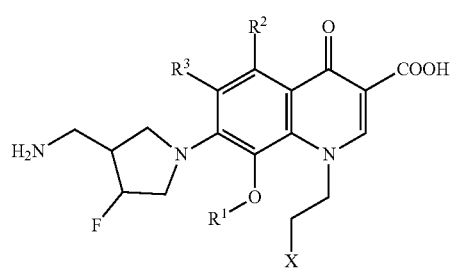

(2)

In the formula (2), $R^1$, $R^2$, $R^3$ and X are defined as described above.

The present inventors have found that precipitation of the compound of the formula (1) or a salt thereof and decomposition of the compound of the formula (1) can be inhibited by adjusting pH of the solution containing particular amounts of the compound of the formula (1) or a salt thereof and the magnesium compound within a specific pH range, and completed the present invention.

The present invention will be described in further detail below.

<1> An aqueous liquid formulation including a compound represented by general formula (1):

[Chemical Formula 3]

(1)

$$\underset{R^4}{\overset{H}{\underset{|}{N}}}\underset{\underset{F}{\overset{}{\bigtriangleup}}}{\overset{R^3}{\underset{}{\bigcirc}}}\underset{R^{1}\overset{}{\diagdown}\mathrm{O}}{\overset{R^2\quad\mathrm{O}}{\underset{}{\bigcirc}}}\underset{X}{\overset{}{\underset{}{\mathrm{COOH}}}}$$

(wherein $R^1$ represents an alkyl group having 1 to 3 carbon atoms which is optionally substituted with one or more substituents selected from the group consisting of a hydrogen atom, a halogen atom, an amino group, a cyano group, and a hydroxyl group, $R^2$ represents a hydrogen atom, a halogen atom, a hydroxyl group, an amino group or an alkyl group having 1 to 3 carbon atoms which is substituted with one or more substituents consisting of a hydrogen atom, a halogen atom, an amino group, a cyano group and a hydroxyl group, $R^3$ represents a hydrogen atom or a halogen atom, $R^4$ represents a hydrogen atom or a halogen atom, and X represents a halogen atom) or a salt thereof, and a magnesium compound, wherein the pH is 5.8 or more and 6.9 or less, and the concentration of the compound represented by the general formula (1) is 3 mg/mL or more.

<2> The aqueous liquid formulation according to <1>, wherein the aqueous liquid formulation is diluted, when it is in use, such that the concentration of the compound represented by the general formula (1) becomes 2 mg/mL or less.

<3> The aqueous liquid formulation according to <1> or <2>, including a hydrochloride of the compound represented by the general formula (1).

<4> The aqueous liquid formulation according to any one of <1> to <3>, wherein the molar ratio of the magnesium compound relative to the compound represented by the general formula (1) or a salt thereof is 0.45 or more and 1.5 or less.

<5> The aqueous liquid formulation according to any one of <1> to <4>, wherein the pH of the aqueous liquid formulation is 5.8 or more and 6.5 or less.

<6> The aqueous liquid formulation according to any one of <1> to <5>, wherein the concentration of the compound represented by the general formula (1) therein is 15 mg/mL or more and 50 mg/mL or less.

<7> The aqueous liquid formulation according to any one of <1> to <6>, wherein the aqueous liquid formulation is diluted, when it is in use, with a saline solution as a dilution liquid.

<8> A method for inhibiting decomposition of a compound represented by general formula (1):

[Chemical Formula 4]

(1)

$$\underset{R^4}{\overset{H}{\underset{|}{N}}}\underset{\underset{F}{\overset{}{\bigtriangleup}}}{\overset{R^3}{\underset{}{\bigcirc}}}\underset{R^{1}\overset{}{\diagdown}\mathrm{O}}{\overset{R^2\quad\mathrm{O}}{\underset{}{\bigcirc}}}\underset{X}{\overset{}{\underset{}{\mathrm{COOH}}}}$$

(wherein $R^1$ represents an alkyl group having 1 to 3 carbon atoms which is optionally substituted with one or more substituents selected from the group consisting of a hydrogen atom, a halogen atom, an amino group, a cyano group, and a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group and a hydroxyl group, $R^3$ represents a hydrogen atom or a halogen atom, $R^4$ represents a hydrogen atom or a halogen atom, and X represents a halogen atom) or a salt thereof, including adding, to an aqueous liquid formulation that contains the compound represented by the general formula (1) or a salt thereof, a magnesium compound of which the molar ratio relative to the compound represented by the general formula (1) or a salt thereof is 0.45 or more and 1.5 or less, and making the concentration of the compound represented by the general formula (1) in the aqueous liquid formulation 3 mg/mL or more.

<9> A manufacturing method of the aqueous liquid formulation according to any one of <1> to <7>, including:

a process (A) of adding a pH adjuster to an aqueous solution of the magnesium compound; and a process (B) of adding, to the aqueous solution obtained in the process (A), the compound represented by the general formula (1) or a salt thereof.

<10> A manufacturing method of the aqueous liquid formulation according to any one of <1> to <7>, including:

a process (C) of dissolving or suspending the compound represented by the general formula (1) or a salt thereof in water while heating at 30° C. or higher and 80° C. or lower; and a process (D) of adding a magnesium compound and a pH adjuster to the aqueous solution or suspension obtained in the process (C).

Advantageous Effects of Invention

According to the present invention, an aqueous liquid formulation that contains the compound of the formula (1) or a salt thereof, in which the precipitation of the compound of the formula (1) or a salt thereof and the decomposition of the compound of the formula (1) are inhibited, can be provided.

Figure 1:
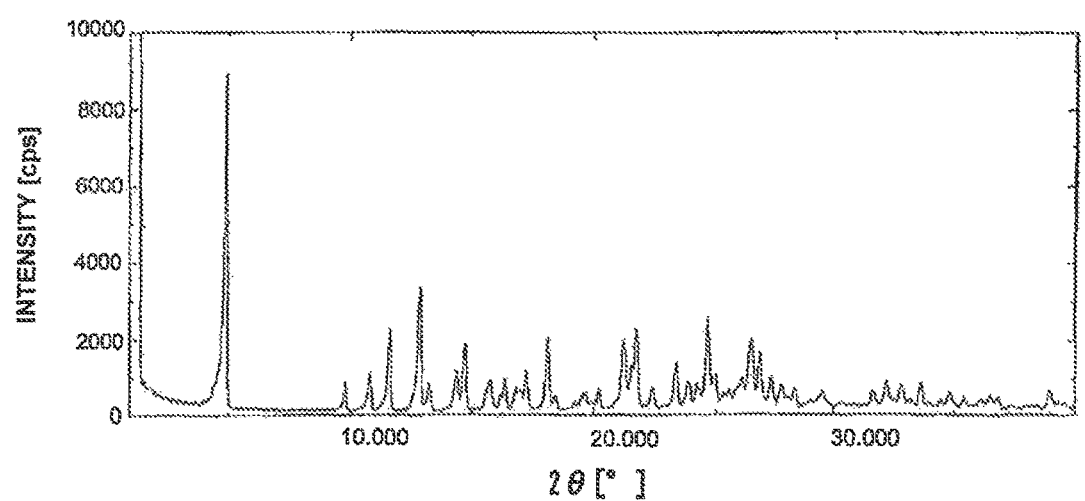
FIG. 1 illustrates a powder X-ray diffraction pattern of A-type crystals of 7-[(3S,4S)-3-{(cyclopropylamino)

methyl}-4-fluoropyrrolidine-1-yl}-6-fluoro-1-(2-fluoro-ethyl)-8-methoxy-4-oxo-1,4-dihydroquinoline-3-carboxylic acid hydrochloride.

FIG. 2 is a table describing peaks having a relative intensity of 0.7 or more when the intensity of the peak at 2θ=4.9 degrees in the diffraction pattern illustrated in FIG. 1 is assumed to be 100.

DESCRIPTION OF EMBODIMENTS

The present embodiment relates to an aqueous liquid formulation that contains a compound represented by general formula (1) or a salt thereof and a magnesium compound.

[Chemical Formula 5]

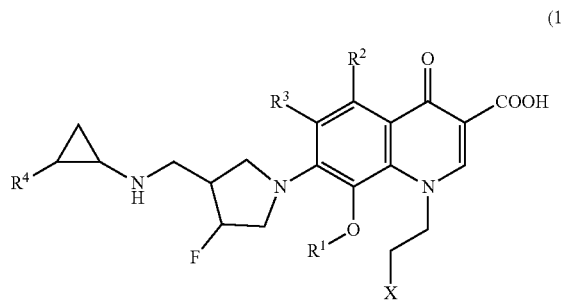

(1)

In the formula (1), $R^1$ represents an alkyl group having 1 to 3 carbon atoms which is optionally substituted with one or more substituents selected from the group consisting of a hydrogen atom, a halogen atom, an amino group, a cyano group, and a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom), wherein the pH is 5.8 or more and 6.9 or less, and the concentration of the compound represented by the formula (1) is 3 mg/mL or more.

The "magnesium compound" described herein is a compound that contains magnesium. Examples of the magnesium compound may include an inorganic magnesium salt such as magnesium chloride, magnesium sulfate, magnesium nitrate, and magnesium phosphate, and an organic magnesium salt such as magnesium citrate, magnesium gluconate, magnesium acetate, and magnesium propionate. For example, as the magnesium compound, one or more of these compounds may be used. The magnesium compound may preferably be an inorganic magnesium salt, and particularly preferably magnesium chloride.

The "aqueous liquid formulation" described herein is a formulation that contains water as base material and is in the form of liquid. Examples thereof may include an injectable formulation, an ophthalmic liquid drug, aqueous nasal drops, aqueous ear drops, and an inhalant liquid drug.

The "injectable formulation" described herein is a sterile formulation to be directly administered to body tissues and organs, such as subcutaneous or intramuscular tissues and blood vessels.

The "dilution liquid" described herein is a solvent or solution used for diluting the aqueous liquid formulation, and represents any solvent or solution that is not harmful when administered to a patient. Examples of the solvent or solution that can be used as the dilution liquid may include water, a saline solution, a Ringer's solution, a glucose solution, a lactate Ringer's solution, an acetate Ringer's solution, a bicarbonate Ringer's solution, a maltose liquid, and a xylitol liquid. One or more of these solvents and solutions may be used as the dilution liquid. The dilution liquid may be particularly preferably a saline solution. When administered to a patient, the aqueous liquid formulation according to the present embodiment is preferably diluted with the dilution liquid so that the concentration of the compound of the formula (1) in the aqueous liquid formulation according to the present embodiment becomes 2 mg/mL or less. The concentration of the compound of the formula (1) when administered may be more preferably 0.5 mg/mL or more and 2 mg/mL or less, and further preferably 1 mg/mL or more and 2 mg/mL or less.

The "halogen atom" described herein represents a fluorine atom, a chlorine atom, a bromine atom, or an iodine atom. Among these, a fluorine atom is preferable. The "alkyl group having 1 to 3 carbon atoms" described herein represents a methyl group, an ethyl group, a propyl group, or a 2-propyl group.

The compound of the formula (1) can be manufactured by, for example, the method described in the WO2005/026147 pamphlet. The compound of the formula (1) contained in the aqueous liquid formulation of the present embodiment may be preferably 7-[3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid, and further preferably 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid. The aqueous liquid formulation of the present embodiment preferably contains a salt of the compound of the formula (1) in terms of the improvement of the solubility to water.

Examples of the salt of the compound of the formula (1) may include a salt formed with an inorganic acid such as hydrochloric acid, hydrobromic acid, sulfuric acid, and phosphoric acid, a salt formed with an organic acid such as maleic acid, fumaric acid, succinic acid, malic acid, malonic acid, methanesulfonic acid, toluenesulfonic acid, benzenesulfonic acid, lactic acid, oxalic acid, acetic acid, trifluoroacetic acid, and tartaric acid, and a salt formed with metal such as sodium, potassium, magnesium, calcium, aluminum, cesium, chromium, cobalt, copper, iron, zinc, platinum, and silver. Among these salts of the compound of the formula (1), a hydrochloride may be particularly preferable from the viewpoint of stability. In particular, a hydrochloride of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid is excellent as a salt of the compound of the formula (1) contained in the aqueous liquid formulation of the present embodiment, because decomposition by light exposure is suppressed, and chemical decomposition is suppressed even when the storage under accelerated test conditions is performed.

The pH of the aqueous liquid formulation of the present embodiment needs to be 5.8 or more and 6.9 or less, in terms of the inhibition of the precipitation of the compound of the formula (1) or a salt thereof during the storage of the aqueous liquid formulation. Furthermore, the aqueous liquid formulation is preferably diluted with the dilution liquid before administered to a patient. In terms of the inhibition of the precipitation of the compound of the formula (1) or a salt thereof during the dilution, the pH of the aqueous liquid formulation of the present embodiment is preferably 5.8 or more and 6.5 or less.

The compound of the formula (1) or a salt thereof is likely to be chemically decomposed to generate a compound (hereinafter, a by-product X) which has an undetermined structure and is difficult to purify, in addition to the compound of the formula (2). In terms of the inhibition of the generation of this by-product X, the concentration of the compound represented by the formula (1) in the aqueous liquid formulation of the present embodiment may be preferably 3 mg/mL or more, more preferably 5 mg/mL or more, further preferably 10 mg/mL or more, more preferably 10 mg/mL or more and 100 mg/mL or less, particularly preferably 15 mg/mL or more and 90 mg/mL or less, and still further preferably 15 mg/mL or more and 50 mg/mL or less. The specific concentration of the compound represented by the formula (1) in the aqueous liquid formulation of the present embodiment may be, for example, 20 mg/mL, 30 mg/mL, or 40 mg/mL.

The above-described "concentration of the compound represented by the formula (1) in the aqueous liquid formulation" is a value obtained by dividing the weight (mg) of the compound of the formula (1) contained in the aqueous liquid formulation by the solvent amount (mL) of the aqueous liquid formulation. It is noted that when a salt of the compound of the formula (1) is used, the above-described "concentration of the compound represented by the formula (1) in the aqueous liquid formulation" is a value obtained by dividing the value (mg) of the weight of the compound of the formula (1) converted from the weight (mg) of the salt of the compound of the formula (1), by the solvent amount (mL).

The use amount of the magnesium compound is not particularly limited. In terms of the improved solubility of the compound of the formula (1) or a salt thereof in water for suppressing the precipitation of the compound of the formula (1) or a salt thereof and the generation of the compound of the formula (2), the molar ratio of the magnesium compound relative to the compound of the formula (1) or a salt thereof may be preferably 0.35 or more, more preferably 0.40 or more, further more preferably 0.45 or more, and still further more preferably 0.70 or more. The "molar ratio of the magnesium compound relative to the compound of the formula (1) or a salt thereof" is a value represented by the formula below:

"molar ratio of magnesium compound relative to compound of formula (1) or salt thereof"=number of moles (mol) of magnesium compound contained in aqueous liquid formulation/number of moles (mol) of compound of formula (1) or salt thereof contained in aqueous liquid formulation.

Also, in consideration of the administration amount per day of the magnesium compound, the "molar ratio of the magnesium compound relative to the compound of the formula (1) or a salt thereof" may be preferably 3.0 or less, more preferably 1.5 or less, and further more preferably 1.1 or less.

The "molar ratio of the magnesium compound relative to the compound of the formula (1) or a salt thereof" is particularly preferably 0.45 or more and 1.5 or less, and further more preferably 0.70 or more and 1.1 or less.

The "pH adjuster" described herein includes an acid, a base, or a buffer. Examples of the pH adjuster may include hydrochloric acid, sulfuric acid, adipic acid or a salt thereof, citric acid or a salt thereof, gluconic acid or a salt thereof, succinic acid or a salt thereof, ascorbic acid or a salt thereof, glacial acetic acid or a salt thereof, acetic acid or a salt thereof, tartaric acid or a salt thereof, fumaric acid or a salt thereof, maleic acid or a salt thereof, lactic acid or a salt thereof, malic acid or a salt thereof, phosphoric acid or a salt thereof, glycine, sodium hydrogen carbonate, sodium carbonate, sodium hydroxide, and magnesium hydroxide. Among these pH adjusters, one or more of these pH adjusters may be used. As the pH preferable adjuster, hydrochloric acid and sodium hydroxide are examplified. Hydrochloric acid and sodium hydroxide may be more preferable. With the pH adjuster, the pH can be adjusted within an appropriate range.

The present invention will be described in further detail below by illustrating a general manufacturing method of the aqueous liquid formulation of the present embodiment. However, this does not limit the scope of the present invention.

The content of the compound represented by the formula (1) in the aqueous liquid formulation of the present embodiment is preferably 500 mg or less, further preferably 10 mg or more and 450 mg or less, further preferably 20 mg or more and 400 mg or less, more preferably 30 mg or more and 200 mg or less, and further more preferably 50 mg or more and 160 mg or less. The content of the compound represented by the formula (1), when a salt of the compound represented by the formula (1) is contained, means a value (mg) obtained by converting the weight (mg) of the salt of the compound represented by the formula (1) into the weight of the compound represented by the formula (1).

The aqueous liquid formulation of the present embodiment is manufactured by, but not particularly limited to, preferably the method as will be described as a general manufacturing method 1 or the method as will be described as a general manufacturing method 2.

(General Manufacturing Method 1)

A magnesium compound is dissolved in a physiologically acceptable carrier such as water, a saline solution, a Ringer's solution, a glucose solution, a lactate Ringer's solution, an acetate Ringer's solution, a bicarbonate Ringer's solution, a maltose liquid, and a xylitol liquid. To the obtained solution, a pH adjuster is added. Thereafter, the compound of the formula (1) or a salt thereof is added. (Here, the molar ratio of the magnesium compound relative to the compound of the formula (1) or a salt thereof is preferably 0.35 or more, and further preferably 0.45 or more and 1.5 or less.) The resultant solution is stirred, so that the compound of the formula (1) or a salt thereof is dissolved. Furthermore, the pH of the solution may be adjusted by the process of adding a pH adjuster to the solution. Also, the amount of the solution may be adjusted by the process of adding a physiologically acceptable carrier to the solution.

By the above-described operation, the aqueous liquid formulation of the present embodiment, which has a pH of 5.8 or more and 6.9 or less and in which the concentration of the compound represented by the formula (1) is 3 mg/mL or more, can be obtained.

(General Manufacturing Method 2)

The compound of the formula (1) or a salt thereof is dissolved or suspended in a physiologically acceptable carrier such as water, a saline solution, a Ringer's solution, a glucose solution, a lactate Ringer's solution, an acetate Ringer's solution, a bicarbonate Ringer's solution, a maltose liquid, and a xylitol liquid. When the obtained solution or suspension is gelled, the solution or suspension may be heated. The temperature of the solution or suspension when heated is preferably 30° C. or higher and 80° C. or lower, further preferably 30° C. or higher and 70° C. or lower, and particularly preferably 30° C. or higher and 50° C. or lower.

To the solution or suspension, a magnesium compound and a pH adjuster are added. The mixture is stirred so that the compound of the formula (1) or a salt thereof is completely dissolved. The pH of the solution may be adjusted by the process of adding a pH adjuster to the solution. Also, the amount of the solution may be adjusted by the process of adding a physiologically acceptable carrier to the solution.

By the above-described operation, the aqueous liquid formulation of the present embodiment, which has a pH of 5.8 or more and 6.9 or less and in which the concentration of the compound represented by formula (1) is 3 mg/mL or more, can be obtained.

EXAMPLES

Although the present invention will be described in further detail with reference to examples below, these examples do not limit the scope of the present invention.

In Examples below, an NMR spectrum was measured using a JNM-EX400 type nuclear magnetic resonance apparatus manufactured by JEOL Ltd. with tetramethyl silane (TMS) as an internal standard. An MS spectrum was measured using JMS-T100LP type and JMS-SX102A type mass spectrometers manufactured by JEOL Ltd. A elemental analysis was performed using a CHN CORDER MT-6 elemental analyzer manufactured by Yanaco Bunseki Kogyo Co.

Also, powder X-ray diffraction was performed using RINT2200 manufactured by Rigaku Corporation. Copper radiation was used as radiation. The measurement condition was a tube current of 36 mA, a tube voltage of 40 kV, a divergence slit of 1 degree, a scattering slit of 1 degree, a receiving slit of 0.15 mm, a scan range of 1 to 40 degrees (2θ), and a scan rate per minute of 2 degrees (2θ).

Reference Example 1

Bis(acetato-O)-{6,7-difluoro-1-(2-fluoroethyl)-8-methoxy-4-oxo-1,4-dihydroquinoline-3-carboxylato-$O^3,O^4$}boron Under nitrogen atmosphere, 103 g (1.67 mol) of boric acid (for the formation of a catalyst) was added to 21.4 L (225 mol) of anhydrous acetic acid. The mixture was heated and stirred at 70.0 to 76.9° C. for 30 minutes (stirring speed: 69.5 rpm). The mixed liquid was cooled to an internal temperature of 24.6° C. Thereafter, 1.01 kg (16.3 mol) of boric acid (first portion) was added to the mixed liquid, and the mixed liquid was stirred at 24.6 to 27.4° C. for 30 minutes. Then, 1.01 kg (16.3 mol) of boric acid (second portion) was added to the mixed liquid, and the mixed liquid was stirred at 24.7 to 27.5° C. for 30 minutes. Next, 1.01 kg (16.3 mol) of boric acid (third portion) was added to the mixed liquid, and the mixed liquid was stirred at 24.7 to 27.7° C. for 30 minutes. Subsequently, 1.01 kg (16.3 mol) of boric acid (forth portin) was added to the mixed liquid, and the mixed liquid was stirred at 25.4 to 29.4° C. for 30 minutes. Furthermore, the mixed liquid was stirred at 50.0 to 56.9° C. for 30 minutes to obtain a boric acid triacetate adjusting liquid.

To the adjusting liquid, 5.50 kg (16.7 mol) of 6,7-difluoro-1-(2-fluoroethyl)-8-methoxy-4-oxo-1,4-dihydroquinoline-3-carboxylic acid ethyl ester was added, and the adjusting liquid was stirred at 54.7 to 56.9° C. for 3 hours. The adjusting liquid was then cooled to 30.0° C., and allowed to stand at room temperature overnight. The resultant adjusting liquid was heated to 58.6° C. to dissolve the precipitate. Then, 16.5 L of acetone was added to the adjusting liquid to obtain a reaction liquid (1).

Under nitrogen atmosphere, a mixed liquid of 193 L of water and 33.7 L (555 mol) of aqueous ammonia (28%) was cooled to −0.6° C. To the mixed liquid, the aforementioned reaction liquid (1) was added, and the vessel for the reaction liquid (1) was washed with 11.0 L of acetone. Thus, the reaction liquid (2) was obtained. The reaction liquid (2) was cooled to 15.0° C., and thereafter stirred at 4.3 to 15.0° C. for one hour. Precipitated crystals were separated by filtration, and washed with 55.0 L of water. Thus, 14.1 kg of wet crude crystals were obtained. The obtained wet crude crystals were dried under reduced pressure at a preset temperature of 65.0° C. for approximately 22 hours to obtain 6.93 kg of crude crystals (yield: 96.7%).

To the obtained crude crystals, 34.7 L of acetone was added under nitrogen atmosphere to prepare a mixed liquid, and the mixed liquid was heated (hot water preset temperature: 57.0° C.) to dissolve the crude crystal. During the heating, 69.3 L of diisopropyl ether was dropped to the mixed liquid until crystallization occurred (dropping amount: 12.0 L). After crystallization was confirmed, the mixed liquid was stirred at 48.3 to 51.7° C. for 15 minutes. Then, the remaining diisopropyl ether was dropped to the mixed liquid, and the mixed liquid was stirred at 45.8 to 49.7° C. for 15 minutes. The mixed liquid was cooled to 15° C., and thereafter stirred at 6.5 to 15.0° C. for 30 minutes. The precipitated crystals were separated by filtration, and washed with 6.93 L of acetone and 13.9 L of diisopropyl ether. Thus, 7.41 kg of wet crystals were obtained. The obtained wet crystals were dried under reduced pressure at a preset temperature of 65.0° C. for approximately 20 hours to obtain 6.47 kg of bis(acetato-O)-{6,7-difluoro-1-(2-fluoroethyl)-8-methoxy-4-oxo-1,4-dihydroquinoline-3-carboxylato-$O^3,O^4$}boron (yield: 90.3%).

Elemental Analysis Value (%): as $C_{17}H_{15}BF_3NO_8$
Calcd.: C, 47.58; H, 3.52; N, 3.26.
Measured: C, 47.41; H, 3.41; N, 3.20.
$^1$H-NMR (CDCl$_3$, 400 MHz) δ: 2.04 (6H, s), 4.21 (3H, d, J=2.9 Hz), 4.88 (2H, dt, J=47.0, 4.4 Hz), 5.21 (2H, dt, J=24.9, 3.9 Hz), 8.17 (1H, t, J=8.8 Hz), 9.10 (1H, s).
ESI MS (positive) m/z: 430 (M+H)$^+$.

Reference Example 2

7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride Under nitrogen atmosphere, 3.56 kg (15.4 mol) of (3R,4S)-3-cyclopropylaminomethyl-4-fluoropyrrolidine, 11.7 L (84.2 mol) of triethylamine, and 30.0 L of dimethylsulfoxide were mixed to obtain a reaction liquid. The reaction liquid was stirred at 23.0 to 26.3° C. for 15 minutes. At 23.0 to 26.3° C., 6.00 kg (14.0 mol) of bis(acetato-O){6,7-difluoro-1-(2-fluoroethyl)-8-methoxy-4-oxo-1,4-dihydroquinoline-3-carboxylato-$O^3,O^4$}boron was added to the reaction liquid. The reaction liquid was stirred at 23.7 to 26.3° C. for 2 hours. To the reaction liquid, 120 L of ethyl acetate was added, and 120 L of water was further added. After that, a solution of 960 g (an amount for obtaining 2 mol/L) of sodium hydroxide and 12.0 L of water was added. After the mixture was stirred for 5 minutes, an aqueous layer was separated. To the aqueous layer, 120 L of ethyl acetate was added. The mixture was stirred for 5 minutes. Then, an ethyl acetate layer was separated.

The portions of the ethyl acetate layer were combined, and 120 L of water was added. The mixture was stirred for 5 minutes, and left to stand. Then, an aqueous layer was removed. The ethyl acetate layer was evaporated under reduced pressure. The obtained residue was dissolved in 60.0 L of 2-propanol, and the solution was allowed to stand at room temperature overnight. A solution of 5.24 L (62.9 mol) of hydrochloric acid and 26.2 L (an amount for obtaining 2 mol/L) of water was added to the obtained 2-propanol solution. The mixed liquid was stirred at 28.2 to 30.0° C. for 30 minutes. The mixed liquid was heated at an outer temperature of 55.0° C. After dissolution (dissolution was confirmed at 47.1°), the mixed liquid was cooled, resulting in crystallization. The mixed liquid was stirred at 39.9 to 41.0° C. for 30 minutes. After cooling (approximately temperature setting: 7.0° C. until 20° C. and −10.0° C. below 20.0° C.), the resultant product was stirred at 2.2 to 10.0° C. for one hour. Precipitated crystals were collected by filtration, and washed with 60 L of 2-propanol to obtain 9.57 kg of wet crude crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride.

Reference Example 3

A-type crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride (compound (1))

To a mixed solvent of 60 L of ethanol and 10.8 L of purified water, 9.57 kg of wet crude crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride was added, and dissolved by heating. This solution was filtered, and the vessel for the solution was washed with a mixed solvent of 24.0 L of ethanol and 1.20 L of purified water. The dissolution was confirmed, and 96.0 L of heated ethanol (99.5) was added to the solution at 71.2 to 72.6° C. This solution was cooled (hot water preset temperature: 60.0° C.), and crystallization was confirmed (crystallization temperature: 61.5° C.). Thereafter, the solution was stirred at 59.4 to 61.5° C. for 30 minutes, and cooled in a stepwise manner (Hot water temperature setting: 40° C. until 50° C., 30° C. until 40° C., 20° C. until 30° C., 7.0° C. until 20.0° C., −10° C. until 15.0° C., and then left to stand), and stirred at 4.8 to 10.0° C. for one hour. Precipitated crystals were separated by filtration, and washed with 30.0 L of ethanol to obtain 5.25 kg of wet crystals of 7-[(3S,4S)-3-{(cyclopropylamino) methyl}-4-fluoropyrrolidine-1-yl]-6-fluoro-1-(2-fluoroethyl)-8-methoxy-4-oxo-1,4-dihydroquinoline-3-carboxylic acid hydrochloride. The obtained wet crystals were dried under reduced pressure at a preset temperature of 50.0° C. for approximately 13 hours to obtain 4.83 kg of the compound (1) (yield: 72.6%).

The result of the powder X-ray diffraction of the compound (1) based on WO2013/069297 is shown in FIGS. 1 and 2. As understood from FIGS. 1 and 2, peaks are observed at 4.9 degrees, 9.8 degrees, 10.8 degrees, 12.9 degrees, 14.7 degrees, 18.2 degrees, 21.7 degrees, 23.4 degrees, 24.7 degrees, and 26.4 degrees, and characteristic peaks can be confirmed at 4.9 degrees, 10.8 degrees, 12.9 degrees, 18.2 degrees, 21.7 degrees, 24.7 degrees and 26.4 degrees. Particularly characteristic peaks can be confirmed at 10.8 degrees, 12.9 degrees, and 24.7 degrees.

Elemental Analysis Value (%): as $C_{21}H_{24}F_3N_3O_4HCl$
Calcd.: C, 53.00; H, 5.30; N, 8.83.
Measured: C, 53.04; H, 5.18; N, 8.83.
$^1$H NMR (DMSO-$d_6$, 400 MHz) δ (ppm): 0.77-0.81 (2H, m), 0.95-1.06 (2H, m), 2.80-2.90 (2H, m), 3.21-3.24 (1H, m), 3.35-3.39 (1H, m), 3.57 (3H, s), 3.65-3.78 (3H, m), 4.13 (1H, dd, J=41.8, 13.1 Hz), 4.64-4.97 (3H, m), 5.14 (1H, dd, J=32.7, 15.6 Hz), 5.50 (1H, d, J=53.7 Hz), 7.80 (1H, d, J=13.7 Hz), 8.86 (1H, s), 9.44 (2H, brs), 15.11 (1H, brs).
ESI MS (positive) m/z: 440 (M+H)$^+$.

(Relationship Between pH and Stability)

Example 1

According to the formulation shown in Table 1, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 0.1 mol/L hydrochloric acid and 0.1 mol/L aqueous sodium hydroxide solution were added to adjust the pH to 5.8. To this solution, water for injection was added so that the total amount became 100 mL. The pH after the amount of the solution was adjusted was 5.8.

It is noted that as water for injection, the water for injection defined in the Japanese Pharmacopoeia 16th Edition was used (the same applies hereinafter).

Example 2

According to the formulation shown in Table 1, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 0.1 mol/L hydrochloric acid and 0.1 mol/L aqueous sodium hydroxide solution were added to adjust the pH to 6.9. To this solution, water for injection was added so that the total amount became 100 mL. The pH after the amount of the solution was adjusted was 6.9.

Comparative Example 1

According to the formulation shown in Table 1, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 0.1 mol/L hydrochloric acid and 0.1 mol/L aqueous sodium hydroxide solution were added to adjust the pH to 5.7. To this solution, water for injection was added so that the total amount became 100 mL. The pH after the amount of the solution was adjusted was 5.7.

Comparative Example 2

According to the formulation shown in Table 1, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 0.1 mol/L hydrochloric acid and 0.1 mol/L aqueous sodium hydroxide solution were added to adjust the pH to 7.0. To this solution, water for injection was added so that the total amount became 100 mL. The pH after the amount of the solution was adjusted was 7.0.

TABLE 1

Prescription

| Components | Comparative Example 1 | Example 1 | Example 2 | Comparative Example 2 |
|---|---|---|---|---|
| Compound (1) | 4.332 g | 4.332 g | 4.332 g | 4.332 g |
| Magnesium chloride hexahydrate | 920 mg | 920 mg | 920 mg | 920 mg |
| 0.1 mol/L hydrochloric acid | As needed | As needed | As needed | As needed |
| 0.1 mol/L aqueous sodium hydroxide solution | As needed | As needed | As needed | As needed |
| Water for injection | As needed | As needed | As needed | As needed |
| (Total) | 100 mL | 100 mL | 100 mL | 100 mL |
| (pH) | 5.7 | 5.8 | 6.9 | 7.0 |

Test Example 1

The aqueous liquid formulation prepared in each of Examples 1 to 2 and Comparative Examples 1 and 2 was measured for the pH and visually observed for appearance. The observation was performed before the storage (that is, immediately after the preparation; the same applies hereinafter) and after the storage of each liquid at 5° C. for one week.

pH measurement method: measured in accordance with the pH measurement method defined in General Test Methods of the Japanese Pharmacopoeia. Observation method: observed using a foreign substance checker (illuminance: 1000 to 2000 lx).

TABLE 2 pH and visual observation result of injectable formulation

| | pH | Before storage | After storage at 5° C. for 1 week |
|---|---|---|---|
| Comparative Example 1 | 5.7 | Slightly yellow, clear liquid | Precipitation of crystals |
| Example 1 | 5.8 | Slightly yellow, clear liquid | Slightly yellow, clear liquid |
| Example 2 | 6.9 | Slightly yellow, clear liquid | Slightly yellow, clear liquid |
| Comparative Example 2 | 7.0 | Precipitation of crystals | Not performed |

As apparent from the test results shown in Table 2, a white precipitate was observed in Comparative Example 1 having a pH of 5.7 and Comparative Example 2 having a pH of 7.0. However, in Example 1 and Example 2 having a pH of 5.8 to 6.9, a precipitate was not precipitated before and after the storage, and the liquid was slightly yellow and clear.

(Relationship Between Concentration and Stability)

Example 3

According to the formulation shown in Table 3, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 8 g of sodium chloride was added. After dissolution, 0.1 mol/L hydrochloric acid and 0.1 mol/L aqueous sodium hydroxide solution were added to adjust the pH to 6.2. To this solution, water for injection was added so that the total amount became 1 L.

Example 4

According to the formulation shown in Table 3, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 3.65 g of sodium chloride was added. After dissolution, 0.1 mol/L hydrochloric acid and 0.1 mol/L aqueous sodium hydroxide solution were added to adjust the pH to 6.2. To this solution, water for injection was added so that the total amount became 500 mL.

Example 5

According to the formulation shown in Table 3, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 0.1 mol/L hydrochloric acid and 0.1 mol/L aqueous sodium hydroxide solution were added to adjust the pH to 6.0. To this solution, water for injection was added so that the total amount became 200 mL.

Comparative Example 3

According to the formulation shown in Table 3, 115 mg of magnesium chloride hexahydrate was dissolved in water for injection. To the solution, 8 mL of 0.1 mol/L aqueous sodium hydroxide solution was added. Thereafter, 541.5 mg of the compound (1) was added and dissolved. To this solution, 8.8 g of sodium chloride was added. After dissolution, 0.1 mol/L hydrochloric acid and 0.1 mol/L aqueous sodium hydroxide solution were added to adjust the pH to 6.2. To this solution, water for injection was added so that the total amount became 1 L.

Comparative Example 4

According to the formulation shown in Table 3, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 17.1 g of sodium chloride was added. After dissolution, 0.1 mol/L hydrochloric acid and 0.1 mol/L aqueous sodium hydroxide solution were added to adjust the pH to 6.2. To this solution, water for injection was added so that the total amount became 2 L.

TABLE 3

| | Prescription | | | | |
|---|---|---|---|---|---|
| Components | Comparative Example 3 | Comparative Example 4 | Example 3 | Example 4 | Example 5 |
| Compound (1) | 541.5 mg | 4.332 g | 4.332 g | 4.332 g | 4.332 g |
| Magnesium chloride hexahydrate | 115 mg | 920 mg | 920 mg | 920 mg | 920 mg |
| Sodium chloride | 8.8 g | 17.1 g | 8 g | 3.65 g | — |
| 0.1 mol/L hydrochloric acid | As needed | As needed | As needed | As needed | As needed |
| 0.1 mol/L aqueous sodium hydroxide solution | As needed | As needed | As needed | As needed | As needed |
| Water for injection | As needed | As needed | As needed | As needed | As needed |
| (Total) | 1 L | 2 L | 1 L | 500 mL | 200 mL |
| (pH) | 6.2 | 6.2 | 6.2 | 6.2 | 6.0 |
| Concentration of compound (1) in injectable formulation (mg/mL)* | 0.5 | 2.0 | 4.0 | 8.0 | 20 |

*A value obtained by dividing value (mg) of weight of free form converted from compound (1) by volume (mL) of water for injection Test Example 2

The aqueous liquid formulation prepared in each of Examples 3 to 5 and Comparative Examples 3 to 4 was stored in a constant-temperature bath at 30±2° C. for 3 months. After the storage, the content of the compound (1) and the content of the by-product X having an undetermined structure were measured by liquid chromatography (Alliance system, manufactured by Waters).
(Condition of Measurement by Liquid Chromatography)
Separation column: a stainless tube having an inner diameter of 4.6 mm and a length of 15 cm was filled with octadecyl silylated silica gel with the size of 3 μm for liquid chromatography. Liquid A: a 1000 mL solution obtained by dissolving 2.16 g of sodium 1-octanesulfonate in diluted phosphoric acid (1→1000)
Liquid B: methanol for liquid chromatography
Flow velocity: 1.0 mL
Detector: UV absorptiometer (measurement wavelength: 294 nm)
Retention time of by-product X relative to retention time of compound of formula (1): 0.64
Liquid sending: the mixing ratio of liquid A and liquid B is shown in Table 4.

TABLE 4

| Mixing ratio between liquid A and liquid B | | |
|---|---|---|
| Analysis time (minute) | Liquid A | Liquid B |
| 0~32 | 56 | 44 |
| 32~50 | 56→30 | 44→70 |
| 50~60 | 30 | 70 |

The content rate of the by-product X is shown in Table 5 as the percentage of the content of the by-product X relative to the content of the compound (1). As apparent from the results in Table 5, when the concentration of the compound (1) in the aqueous liquid formulation became higher, the content rate of the by-product X after the storage at 30° C. for 3 months decreased. Specifically, the content rate of the by-product X was lower in Examples 3 to 5 in which the concentration of the compound (1) was 3 mg/mL or more, compared to those in Comparative Examples 3 and 4 in which the concentration of the compound (1) was less than 3 mg/mL. Furthermore, it can be understood that the generation of the by-product X is further inhibited in Example 5 in which the concentration of the compound (1) is 10 mg/mL or more, compared to Example 3 (4.0 mg/mL) and Example 4 (8.0 mg/mL).

Example 6

According to the formulation shown in Table 6, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 0.1 mol/L hydrochloric acid and 0.1 mol/L aqueous sodium hydroxide solution were added to adjust the pH to 6.0. To this solution, water for injection was added so that the total amount became 200 mL.

Example 7

According to the formulation shown in Table 6, 920 mg of magnesium chloride hexahydrate was dissolved in water for injection. To the solution, 8 mL of 0.1 mol/L aqueous sodium hydroxide solution was added. Thereafter, 4.332 g of

TABLE 5

| Purity test result | | | | | | |
|---|---|---|---|---|---|---|
| | | Comparative Example 3 | Comparative Example 4 | Example 3 | Example 4 | Example 5 |
| Concentration of compound (1) in injectable formulation (mg/mL) | | 0.5 | 2.0 | 4.0 | 8.0 | 20 |
| Content rate (%) of by-product X | Before storage | 0.04 | 0.04 | 0.04 | 0.04 | 0.04 |
| | After storage at 30° C. for 3 months | 0.18 | 0.16 | 0.13 | 0.13 | 0.11 | the compound (1) was added and dissolved. To this solution, 0.1 mol/L hydrochloric acid and 0.1 mol/L aqueous sodium hydroxide solution were added to adjust the pH to 6.0. To this solution, water for injection was added so that the total amount became 100 mL.

Comparative Example 5

According to the formulation shown in Table 6, 920 mg of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 17.1 g of sodium chloride was added. After dissolution, 0.1 mol/L hydrochloric acid and 0.1 mol/L aqueous sodium hydroxide solution were added to adjust the pH to 6.5. To this solution, water for injection was added so that the total amount became 2 L.

TABLE 6

| | Prescription | | |
|---|---|---|---|
| Components | Comparative Example 5 | Example 6 | Example 7 |
| Compound (1) | 4.332 g | 4.332 g | 4.332 g |
| Magnesium chloride hexahydrate | 920 mg | 920 mg | 920 mg |
| Sodium chloride | 17.1 g | — | — |
| 0.1 mol/L hydrochloric acid | As needed | As needed | As needed |
| 0.1 mol/L aqueous sodium hydroxide solution | As needed | As needed | As needed |
| Water for injection | As needed | As needed | As needed |
| (Total) | 2 L | 200 mL | 100 mL |
| (pH) | 6.5 | 6.0 | 6.0 |
| Concentration of compound (1) in injectable formulation* | 2.0 | 20 | 40 |

*A value obtained by dividing value (mg) of weight of free form converted from compound (1) by volume (mL) of water for injection Test Example 3

The aqueous liquid formulation prepared in each of Examples 6 to 7 and Comparative Example 5 was stored in a constant-temperature bath at 40±2° C. for 3 months. After the storage, the content of the compound (1) and the content of the by-product X were measured by liquid chromatography (Alliance system, manufactured by Waters), in the same method as that in Test Example 2.

TABLE 7

| | Purity test result | | |
|---|---|---|---|
| Components | Comparative Example 5 | Example 6 | Example 7 |
| Concentration of compound (1) in injectable formulation (mg/mL)* | 2.0 | 20 | 40 |
| Content rate (%) of by-product X Before storage | 0.04 | 0.04 | 0.04 |
| After storage at 40° C. for 3 months | 0.45 | 0.34 | 0.31 |

*A value obtained by dividing value (mg) of weight of free form converted from compound (1) by volume (mL) of water for injection The content rate of the by-product X is shown in Table 7 as the percentage of the content of the by-product X relative to the content of the compound (1). As apparent from the results in Table 7, it became clear that when the concentration of the compound (1) became higher, the content rate of the by-product X after the storage at 40° C. for 3 months decreased.

(Relationship Between Magnesium Chloride and Stability)

Example 8

According to the formulation shown in Table 8, 1.39 g of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 0.1 mol/L hydrochloric acid and 0.1 mol/L aqueous sodium hydroxide solution were added to adjust the pH to 6.0. To this solution, water for injection was added so that the total amount became 100 mL.

Example 9

According to the formulation shown in Table 8, 1.85 g of magnesium chloride hexahydrate was dissolved in water for injection. To the solution, 8 mL of 0.1 mol/L aqueous sodium hydroxide solution was added. Thereafter, 4.332 g of the compound (1) was added and dissolved. To this solution, 0.1 mol/L hydrochloric acid and 0.1 mol/L aqueous sodium hydroxide solution were added to adjust the pH to 6.0. To this solution, water for injection was added so that the total amount became 100 mL.

TABLE 8

| | Prescription | | |
|---|---|---|---|
| Components | Example 7 | Example 8 | Example 9 |
| Compound (1) | 4.332 g | 4.332 g | 4.332 g |
| Magnesium chloride hexahydrate | 920 mg | 1.39 g | 1.85 g |
| 0.1 mol/L hydrochloric acid | As needed | As needed | As needed |
| 0.1 mol/L aqueous sodium hydroxide solution | As needed | As needed | As needed |
| Water for injection | As needed | As needed | As needed |
| (Total) | 100 mL | 100 mL | 100 mL |
| (pH) | 6.0 | 6.0 | 6.0 |

Test Example 4

The aqueous liquid formulation prepared in each of Examples 7 to 9 was stored in a constant-temperature bath at 40±2° C. for 4 weeks. Then, the content of 7-{(3S,4S)-3-amino methyl-4-fluoropyrrolidine-1-yl}-6-fluoro-1-(2-fluoroethyl)-8-methoxy-4-oxo-1,4-dihydroquinoline-3-carboxylic acid (the compound (2)) and the content of the compound (1) were measured by liquid chromatography (Alliance system, manufactured by Waters). The liquid chromatography was performed under a condition similar to Test Example 2.

Retention time of compound (2) relative to retention time of compound (1): 0.69

TABLE 9

| | Purity test result of injectable formulation | | |
|---|---|---|---|
| Components | Example 7 | Example 8 | Example 9 |
| Molar ratio of magnesium compound to compound (1) | 0.50 | 0.75 | 1.0 |
| Content rate (%) of compound (2) Before storage | 0.02 | 0.00 | 0.00 |
| After storage at 40° C. for 4 weeks | 0.74 | 0.44 | 0.35 |

The content rate of the compound (2) is shown in Table 9 as the percentage of the content of the compound (2) relative to the content of the compound (1). As apparent from the results in Table 9, the generated amount of the compound (2) could be reduced by increasing the content of magnesium chloride in the aqueous liquid formulation to increase the molar ratio of the magnesium compound relative to the compound (1).

(Manufacturing Time)

Example 10

To water for injection, 4.332 g of the compound (1) was added while heating to 40° C. To the mixture, 920 mg of magnesium chloride hexahydrate was added. Then, 8 mL of 0.1 mol/L sodium hydroxide was added and dissolved. To this solution, 0.1 mol/L hydrochloric acid and 0.1 mol/L sodium hydroxide solution were added to adjust the pH to 6.0. To this solution, water for injection was added so that the total amount became 100 mL.

Example 11

To water for injection, 4.332 g of the compound (1) was added. To the liquid, 920 mg of magnesium chloride hexahydrate was added. Then, 0.1 mol/L sodium hydroxide was added to adjust the pH to 6.0 and dissolved. To this solution, 0.1 mol/L hydrochloric acid and a 0.1 mol/L sodium hydroxide solution were added to adjust the pH to 6.0. To this solution, water for injection was added so that the total amount became 100 mL.

Test Example 5

The manufacturing time in each of Example 7, Example 10, and Example 11 was measured.

TABLE 10

Result of manufacturing time for injectable formulation

| | Example 7 | Example 10 | Example 11 |
|---|---|---|---|
| Manufacturing time | 56 min | 51 min | 186 min |

The manufacturing time in each manufacturing method is shown in Table 10. The compound (1) has the property of being gelled when being brought into contact with water. When the compound (1) is added to water as in Example 11, the compound (1) is gelled to become in an unmixed state (lump). Thus, stirring needs to be continued for as long as 3 hours until the compound (1) is uniformly mixed with water. When the manufacturing time becomes longer, manufacturing costs such as abrasion of manufacturing facility and labor costs unfavorably increase.

On the other hand, the gelation can be reduced by previously adding magnesium chloride hexahydrate to water to which the compound (1) is to be added and adjusting the pH to a value within an appropriate range. As apparent from the manufacturing time of Example 7, the compound (1) is quickly dissolved in water, and the manufacturing time can be ⅓ or less of that of Example 11. Also, when the compound (1) is added to water, the manufacturing time can also be shortened by heating (Example 10).

INDUSTRIAL APPLICABILITY

An aqueous liquid formulation that contains the compound of the formula (1) or a salt thereof, and that has an excellent antibacterial activity against Gram-positive bacteria and Gram-negative bacteria is provided. The aqueous liquid formulation of the present invention, in which the precipitation and chemical decomposition of the compound of the formula (1) is suppressed, is industrially useful.

The invention claimed is:

1. An aqueous liquid formulation comprising
7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof, and a magnesium compound, wherein
the aqueous liquid formulation has a pH of 5.8 or more and 6.9 or less, and
7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid is contained in a concentration of 3 mg/mL or more.

2. The aqueous liquid formulation according to claim 1, wherein the aqueous liquid formulation is diluted, when the aqueous liquid formulation is in use, such that the concentration of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid becomes 2 mg/mL or less.

3. The aqueous liquid formulation according to claim 1, comprising a hydrochloride of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid.

4. The aqueous liquid formulation according to claim 1, wherein a molar ratio of the magnesium compound relative to 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof is 0.45 or more and 1.5 or less.

5. The aqueous liquid formulation according to claim 1, wherein the pH of the aqueous liquid formulation is 5.8 or more and 6.5 or less.

6. The aqueous liquid formulation according to claim 1, wherein the concentration of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid in the aqueous liquid formulation is 15 mg/mL or more and 50 mg/mL or less.

7. The aqueous liquid formulation according to claim 1, wherein the aqueous liquid formulation is diluted, when the aqueous liquid formulation is in use, with a saline solution as a dilution liquid.

8. A method for inhibiting decomposition of a compound represented by general formula (1):

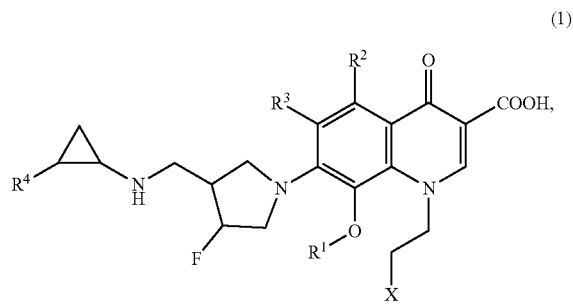

(1)

(wherein $R^1$ represents an alkyl group having 1 to 3 carbon atoms which is optionally substituted with one or more substituents selected from the group consisting of a hydrogen atom, a halogen atom, an amino group, a cyano group, and a hydroxyl group, $R^2$ represents a hydrogen atom, a halogen atom, a hydroxyl group, an amino group, or an alkyl group having 1 to 3 carbon atoms which is optionally substituted with one or more substituents selected from the group consisting of a hydrogen atom, a halogen atom, an amino group, a cyano group and a hydroxyl group, $R^3$ represents a hydrogen atom or a halogen atom, $R^4$ represents a hydrogen atom or a halogen atom, and X represents a halogen atom, or a salt thereof, comprising adding, to an aqueous liquid formulation that contains the compound represented by the general formula (1) or a salt thereof, a magnesium compound of which a molar ratio relative to the compound represented by the general formula (1) or a salt thereof is 0.45 or more and 1.5 or less, and making the concentration of the compound represented by the general formula (1) in the aqueous liquid formulation 3 mg/mL or more.

9. A manufacturing method of the aqueous liquid formulation according to claim 1, comprising:

a process (A) of adding a pH adjuster to an aqueous solution of a magnesium compound; and a process (B) of adding, to the aqueous solution obtained in the process (A), 7-[(3S,4S)-3-{(cyclopropylamino) methyl}-4-fluoropyrrolidine-1-yl]-6-fluoro-1-(2-fluoroethyl)-8-methoxy-4-oxo-1,4-dihydroquinoline-3-carboxylic acid or a salt thereof.

10. A manufacturing method of the aqueous liquid formulation according to claim 1, comprising:

a process (C) of dissolving or suspending 7-[(3 S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof in water while heating at 30° C. or higher and 80° C. or lower; and a process (D) of adding a magnesium compound and a pH adjuster to the aqueous solution or suspension obtained in the process (C).

* * * * *